United States Patent
Gokaraju et al.

(10) Patent No.: US 7,208,615 B2
(45) Date of Patent: Apr. 24, 2007

(54) TRIPLE MINERAL SALTS OF (-)-HYDROXYCITRIC ACID AND PROCESSES FOR PREPARING THE SAME

(75) Inventors: Ganga Raju Gokaraju, Andhra Pradesh (IN); Rama Raju Gokaraju, Andhra Pradesh (IN); Venkata Subbaraju Gottumukkala, Andhra Pradesh (IN); Venkateswarlu Somepalli, Andhra Pradesh (IN)

(73) Assignee: Laila Impex, Andhra Pradesh (IN)

( * ) Notice: Subject to any disclaimer, the term of this patent is extended or adjusted under 35 U.S.C. 154(b) by 237 days.

(21) Appl. No.: 10/525,210

(22) PCT Filed: Mar. 9, 2004

(86) PCT No.: PCT/IN2004/000056

§ 371 (c)(1),
(2), (4) Date: Feb. 22, 2005

(87) PCT Pub. No.: WO2005/085164

PCT Pub. Date: Sep. 15, 2005

(65) Prior Publication Data

US 2006/0240074 A1   Oct. 26, 2006

(51) Int. Cl.
C07F 3/00   (2006.01)
A61K 47/00   (2006.01)
C07C 51/42   (2006.01)

(52) U.S. Cl. .................. 556/133; 562/580; 514/574; 424/439

(58) Field of Classification Search ............... 556/133; 514/574; 562/580; 424/439
See application file for complete search history.

(56) References Cited

U.S. PATENT DOCUMENTS

| | | | |
|---|---|---|---|
| 5,656,314 A | 8/1997 | Moffett et al. | |
| 6,221,901 B1 | 4/2001 | Shrivastava et al. | |
| 6,395,296 B1 | 5/2002 | Balasubramanyam et al. | |
| 2005/0282894 A1* | 12/2005 | Raju | 514/554 |
| 2006/0106101 A1* | 5/2006 | Gokaraju et al. | 514/494 |

OTHER PUBLICATIONS

International Search Report mailed Oct. 12, 2004.

* cited by examiner

*Primary Examiner*—Porfirio Nazario-Gonzalez
(74) *Attorney, Agent, or Firm*—Rader, Fishman & Grauer PLLC

(57) ABSTRACT

This invention relates to novel triple salts of (−)-hydroxycitric acid having the general formula 1

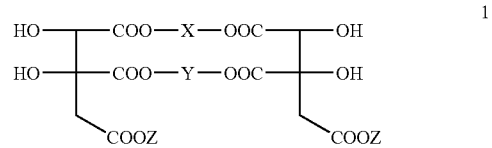

wherein X, Y are selected from zinc or group IIA metal and Z is selected from group IA metal of the Periodic Table.

Preferred salts are triple metal salts of calcium, magnesium or zinc and potassium.

This invention also includes a process for preparing the triple salts by adding stiochiometric amounts of aqueous solutions of the compounds of the desired metal to an aqueous solution of (−)-HCA. Preferably an extract from *garcinia* fruit ring is used as a starting material.

Compounds of this invention are substantially tasteless, odorless and highly water soluble and find use in beverages and in neutraceuticals.

15 Claims, 2 Drawing Sheets

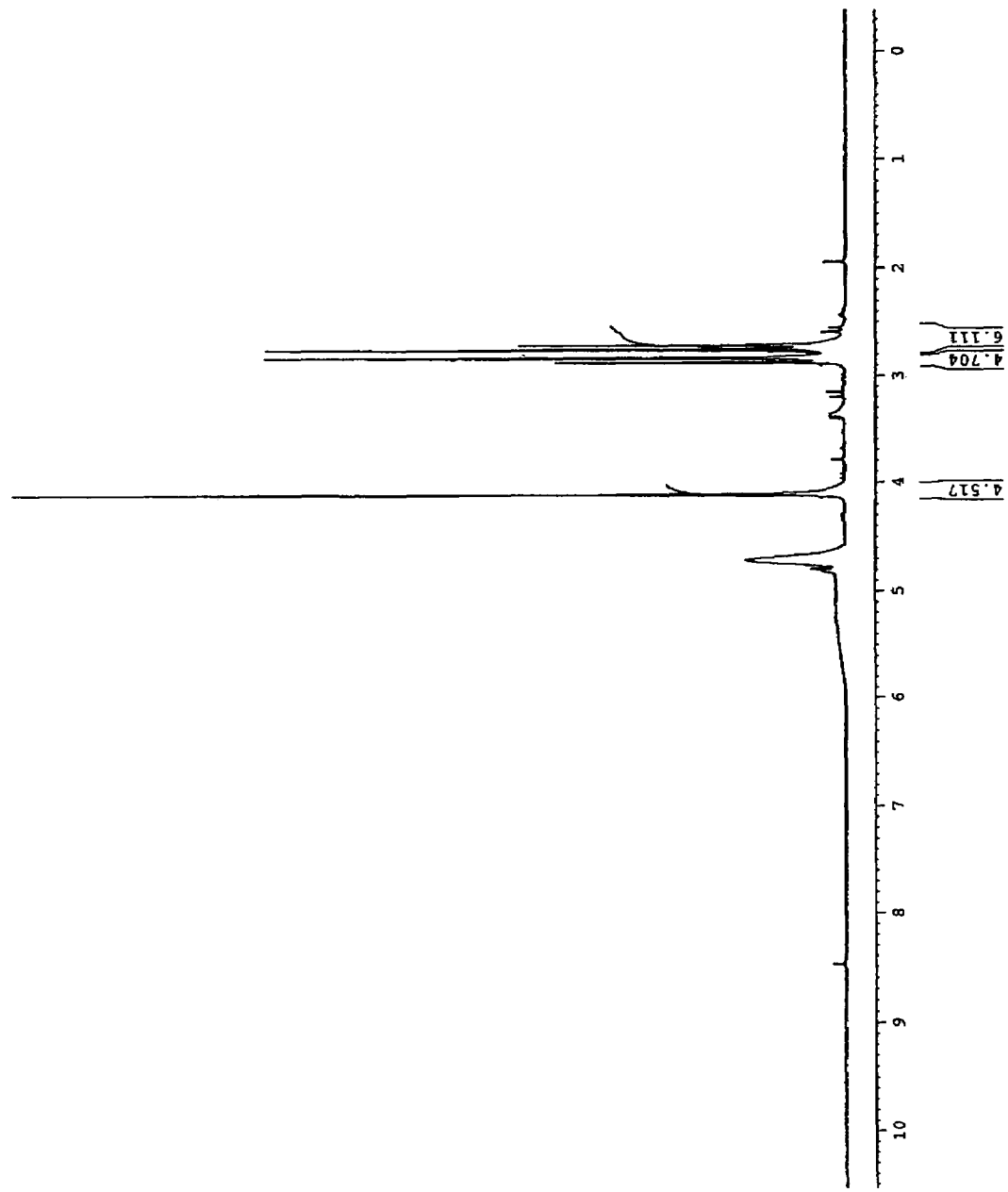

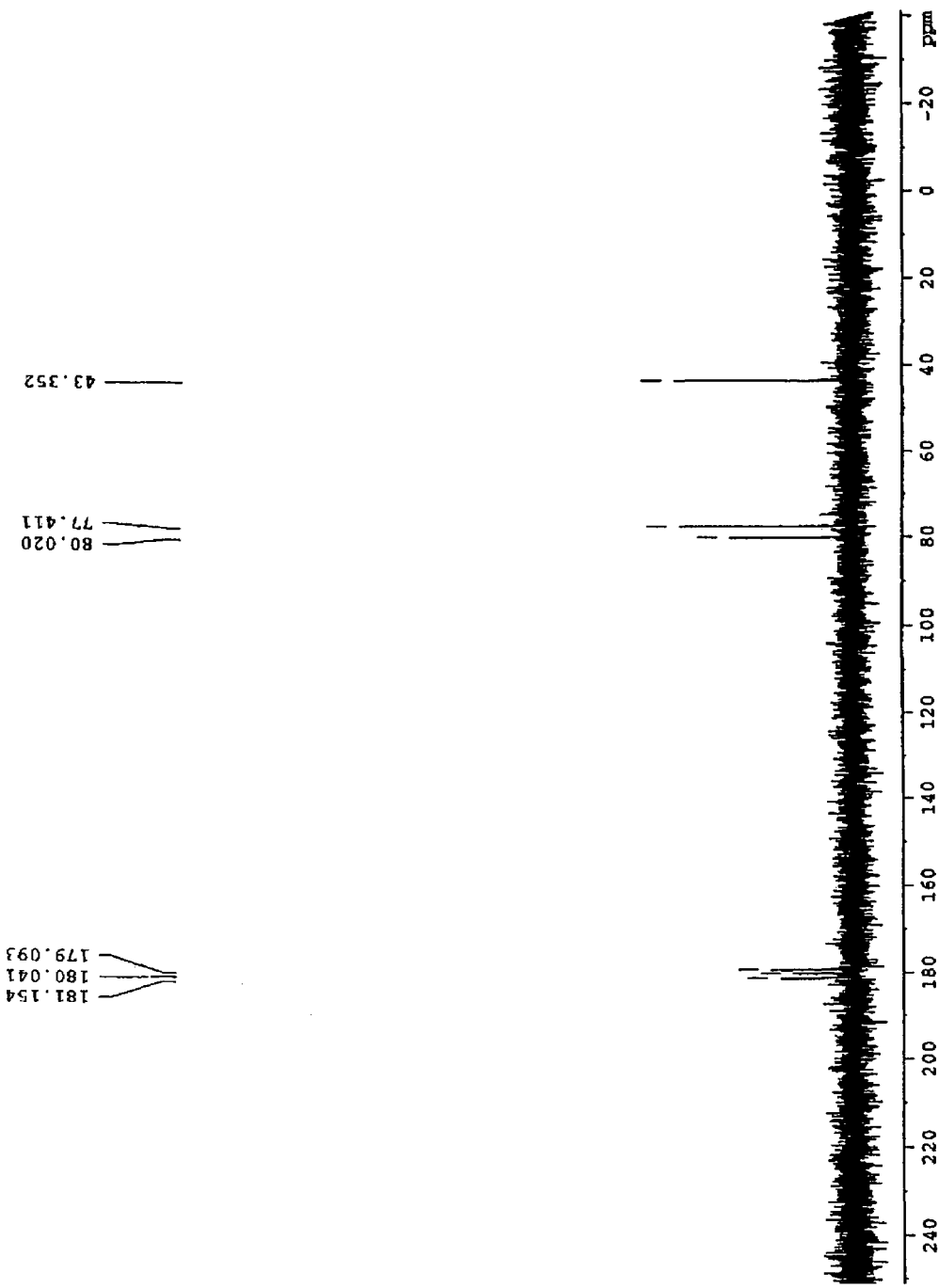
Figure-2: ¹³C NMR spectrum (100 MHz, D₂O) of HCA Ca/ Mg/ K salt

TRIPLE MINERAL SALTS OF (−)-HYDROXYCITRIC ACID AND PROCESSES FOR PREPARING THE SAME

This invention relates to novel triple mineral salts of (−)-hydroxycitric acid and processes for preparing the same. These salts are valuable nutraceuticals and dietary supplements. Compounds of particular relevance are triple salts of hydroxycitric acid containing calcium, magnesium or zinc and potassium.

TECHNICAL FIELD OF THE INVENTION

The (−)-hydroxycitric acid (HCA) is a naturally occurring acid found in the rinds of the fruit of *Garcinia cambogia*, *Garcinia indica* and *Garcinia mangostana*. The dried fruit rind of *G. cambogia*, also known as Malabar tamarind, is commonly used in Southeast Asia (particularly southern India) as a food preservative, flavoring agent and carminative. The primary mechanism of action of (−)-HCA appears to be related to act as a competitive inhibitor of the enzyme ATP-citrate lyase, which catalyzes the conversion of citrate and coenzyme A to oxaloacetate and acetyl coenzyme A (acetyl-CoA). Extensive experimental studies suggest that (−)-HCA suppresses the fatty acid synthesis, lipogenesis and food intake thus leading to weight reduction. In addition to suppression of fatty acid and fat synthesis, (−)-HCA is thought to suppress food intake via loss of appetite by stimulation of liver gluconeogenesis. Various researchers have evaluated HCA for its weight control properties, fat burning properties, lipid level lowering effect, appetite regulation, metabolic rate increase and other effects. A number of patents have been granted based on the above studies and various methods of extraction of HCA from the fruit. The isolation and chemical nature of (−)-hydroxycitric acid from *Garcinia* rind are described in the publication of Lewis, Y. S. et al, Phytochemistry, 1965, 4, 619–625. Moffett, et al., U.S. Pat. No. 5,656,314 (1997) described a process for the aqueous extraction of (−)-HCA from *Garcinia* rinds.

BACKGROUND ART

It has been found that the free acid form of (−)-hydroxycitric acid is unstable, forming lactone (FIG. 1) which generally do not possess the desired bioactivity and also the liquid form of HCA tends to be unstable during storage. Therefore, food preparations that incorporate the free acid in liquid form will not provide the full benefit of the HCA in the final preparation.

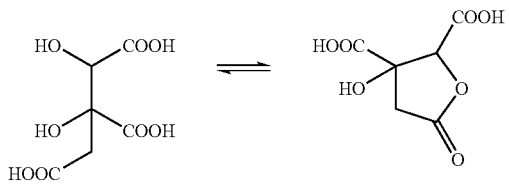

FIG. 1

A number of patents have been granted for the preparation of (−)-hydroxycitric acid salts. Singh, et al., Biol. Memoirs, 1995, 21, 27–33, describes the preparation of calcium salt of HCA. The drawback of this salt is not very soluble in water. Majeed, et al., U.S. Pat. No. 5,783,603 (1998), disclosed the preparation of potassium salt of HCA, but it is hygroscopic and has strong pungent taste. Ganga Raju, G. PCT Publication No. WO 99/03464 (28 Jan. 1999) described the preparation of calcium and potassium or sodium double salts of HCA and its use as dietary supplements and food products to reduce body weight. Balasubramanyam, et al., U.S. Pat. No. 6,160,172 (2000), disclosed the preparation of similar double salts of HCA.

Calcium gives bones their strength, while magnesium helps them maintain their elasticity to prevent injury. The more calcium in the diet, the more magnesium that is needed. Calcium given alone can induce a magnesium deficiency. The most serious complications from a deficiency of magnesium are heart conditions such as irregular heartbeat and rapid heartbeat (Bariscode, M. et al., American Journal of Nutrition, 1996, 19, 296). The magnesium recommended in USA by the Daily Reference Intake (DRI) is 420 mg for males and 330 mg for females. So it is good to have good calcium and magnesium in our daily diet or supplement. Shrivatstava, et al, U.S. Pat. No. 6,221,901 (2001) disclosed the magnesium (−) hydroxycitrate as dietary nutritional supplement.

Zinc is an essential mineral that is found in almost every cell. It is needed for wound healing, sense of taste and smell, DNA synthesis and it supports normal growth and development during pregnancy, childhood and adolescence. The DRI's of zinc for adult male is 11 mg and for adult female is 8 mg.

There exits a need for a stable and highly water soluble (−)-hydroxycitric acid salts that overcome the above drawbacks of insolubility, pungent taste and should have more number of desired minerals for health benefit.

OBJECTS OF THIS INVENTION

A stable highly water soluble salt of hydroxycitric acid that contains essential trace minerals as dietary supplements as well as processes for preparing such salts are the objectives of this invention.

DISCLOSURE OF THE INVENTION

It has been found that novel triple salts of (−)-hydroxycitric acid having the following general formula 1 show good stability and high water solubility.

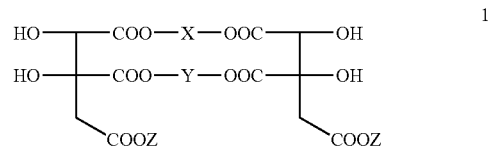

wherein X, Y are selected from zinc or group IIA metal and Z is selected from group IA metal of the Periodic Table.

wherein X, Y and Z are preferred compounds of this invention are expressed by the following general formula 2

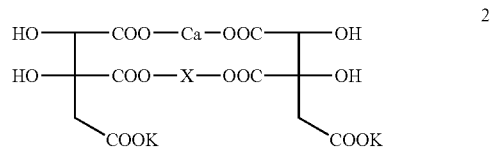

wherein X represents magnesium or zinc

The new triple salts according to this invention may be prepared by the following processes:
(a) The purified (−)-hydroxycitric acid is reacting with magnesium or zinc compound and calcium compound and finally with potassium compound.
(b) by reacting calcium hydroxycitrate with magnesium compound and potassium compound.
(c) by reacting equimolar amounts of calcium hydroxycitrate, magnesium hydroxycitrate and potassium hydroxycitrate.

In the first process, purified (−)-hydroxycitric acid is prepared by treating the calcium hydroxycitrate obtained from water extract of the *Garcinia* fruit with phosphoric acid (Ganga Raju, G, PCT Publication No. WO 99/03464) or passing the water extract of the *Garcinia* fruit through anion exchange resin followed by passing through cation exchange column (U.S. Pat. No. 6,160,172). This purified (−)-HCA is reacting with stoichiometric quantities of a magnesium compound, a calcium compound and a potassium compound. After charcoal treatment, the salt is recovered by spray drying. Although the structure of the resultant product is not known with certainty, a likely structural formula for the preferred product is shown above (formula 2).

In the second process, the suspension of calcium hydroxycitrate is reacting with aqueous magnesium carbonate followed by aqueous potassium hydroxide solution. After charcoal treatment of the clear solution is spray dried.

According to third process, the aqueous tripotassium hydroxycitrate (U.S. Pat. No. 6,447,807) is reacting with equimolar amounts of calcium hydroxycitrate and magnesium hydroxycitrate (U.S. Pat. No. 6,221,901)

Preferred metals selected are calcium, magnesium or zinc and potassium and these metal compounds are selected from their corresponding carbonates or hydroxides.

The preferred triple salts of calcium, magnesium and potassium of HCA has approximately 65% to 75% of HCA, 4–9% of calcium, 2–5% of magnesium and between 14 to 20% of potassium. Other preferred metals are Be, Sr, Ba, Ra in the form of carbonates, hydroxides or oxides. Group 1A metals are Li, Na, K, Rb, Cs, Fr in the form of their carbonates, oxides and hydroxides.

Novel triple salts of this invention are stable, highly water soluble and has no pungent taste. The salts of the present invention have effective amounts of the minerals, particularly potassium, magnesium or zinc and calcium and enhances efficient absorption of these essential nutrients by the system.

Structural Analysis of the Calcium, Magnesium and Potassium Triple Salt of (−)-HCA

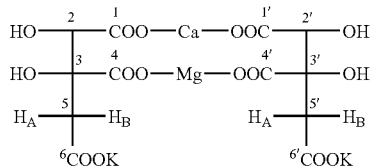

The structure of the calcium, magnesium and potassium triple salt of (−)-HCA was confirmed by its $^1H$ NMR and $^{13}C$ NMR data. The $^1H$ NMR signals (FIG. 1) of methylene protons ($H_A$-5, H-5' & $H_B$-5, H-5') appeared at δ 2.73, 2.85 as two doublets with large coupling constants (16.5 Hz) characteristic of geminal protons and a signlet at δ 4.11 corresponding to methine protons (H-2, H-2'; Table-1). In $^{13}C$ NMR spectrum (FIG. 2) the peaks at δ 43.35, 77.41 & 80.02 could be assigned to methylene carbons (C-5, C-5'), methine carbons (C-2, C-2') and quaternary carbons (C-3, C-3') respectively. The peaks at δ 179.09, 180.04, 181.15 corresponds to carbonyl carbons (C-1, C-1', C-4, C-4', C-6 and C-6') of the carboxylate groups. The metals, calcium, and magnesium were estimated by EDTA-titrimetric method and potassium was estimated by flame-photometric method (Jeffery, G. H., Bassett, J., Mendham, J., Denney, R. C. in: Vogel's text book of Quantitative Chemical Analysis, Fifth Ed.; ELBS: UK, 1989). The analytical data of the representative salt was found to be calcium: 6.06%, magnesium: 3.6% and potassium: 18.9%.

TABLE 1

Proton NMR spectral data of calcium, magnesium and potassium triple salt of (−)-HCA

| S. No. | δ H(D$_2$O) | Assignment |
|---|---|---|
| 1 | 2.73(d, J=16.5Hz) | $H_A$-5,5' |
| 2 | 2.85(d, J=16.5Hz) | $H_B$-5,5' |
| 3 | 4.11(s) | H-2,2' |

TABLE 2

Carbon NMR spectral data of calcium, magnesium and potassium triple salt of (−)-HCA

| S. No. | δ C(D$_2$O) | Assignment |
|---|---|---|
| 1 | 43.35 | C-5,5' |
| 2 | 77.41 | C-2,2' |
| 3 | 80.02 | C-3,3' |
| 4 | 179.09 | C-1,1' |
| 5 | 180.04 | C-4,4' |
| 6 | 181.15 | C-6,6' |

DESCRIPTION OF THE PREFERRED EMBODIMENTS

The following examples describe the preferred embodiments of the processes of preparing the triple salts of (−)-hydroxycitric acid.

Example: 1

Calcium, magnesium and potassium triple salt of HCA: To an aqueous purified extract of *garcinia* solution (36 mL, 2.0 g, 1.0 molar equivalent) was added magnesium carbonate (460 mg, 0.5 molar equivalent) and stirred for 15 min. Then calcium hydroxide (350 mg, 0.5 molar equivalent) was added and after stirring for 15 min, potassium hydroxide (530 mg, 1.0 molar equivalent) was also added and stirred for 5 min. The pH of the solution was adjusted to 11 using potassium hydroxide solution and after stirring for 2 h, the pH of the solution was adjusted back to 7.0 using *garcinia* solution. Charcoal (1.0 g) was added and after stirring for 10 min. the solution was filtered through celite and evaporated to obtain a colourless triple salt of HCA (3.7 g).

The analysis showed that HCA is 66.14%; lactone is 0.5%: calcium is 6.06%, magnesium is 3.6% and potassium is 18.9%.

Example: 2

Calcium, magnesium and potassium triple salt of HCA: To an aqueous purified extract of *garcinia* solution (30 mL, 2.0 g, 1.0 molar equivalent) was added potassium hydroxide (1.6 g, 3.0 molar equivalent) and stirred for 1 h. Then calcium hydroxycitrate (1.1 g) and magnesium hydroxycitrate (1.1 g) were added and stirred 2 h. To the clear reaction mixture, charcoal (2.0 g) was added and heated at 70–80° C. and the solution was filtered through celite and evaporated to obtain a colourless triple salt of HCA (4.5 g).

The analysis showed that HCA is 68.13%; lactone is 0.56%; calcium is 5.05%, magnesium is 2.60% and potassium is 19.30%.

Example: 3

Calcium, zinc and potassium triple salt of HCA: To an aqueous purified extract of *garcinia* solution (27 mL, 2.0 g, 1.0 molar equivalent) was added zinc carbonate (0.52 g, 0.5 molar equivalent) and stirred for 10 min. Then calcium hydroxide (354 mg, 0.5 molar equivalent) was added and after stirring for 30 min, potassium hydroxide (530 mg, 1.0 molar equivalent) was added and stirred for 10 min. The pH of the solution was adjusted to 11 using aqueous potassium hydroxide solution and stirred for 2 h. After stirring for 2 h, pH was adjusted back to 7.0 using *garcinia* solution and charcoal (1.0 g) was added and stirred for 10 min. The solution was filtered through celite and water was evaporated to obtain a colourless triple salt of HCA (3.0 g).

The analysis showed that HCA is 65.28%; lactone is 0.5%: calcium is 5.66%, zinc is 6.97% and potassium is 18.17%.

Purity level of the salts prepared by these examples are above 95%. The above examples are only illustrative in nature, obvious equivalents and modifications are within the scope of the appended claims.

The invention claimed is:

1. Triple metal salts of (−)-hydroxycitric acid having the general formula 1

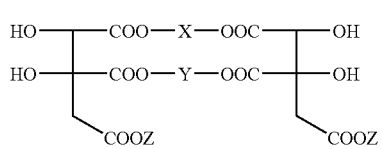

wherein X and Y are selected from zinc or group IIA metals, and Z is selected from group IA metals of the Periodic Table.

2. Triple metal salts of (−)-hydroxycitric acid having the formula 2

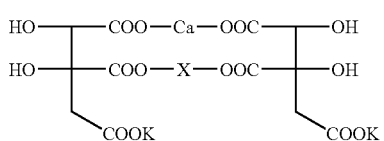

wherein X is magnesium or zinc.

3. The triple metal salts of (−)-hydroxycitric acid as claimed in claims 1 or 2, wherein at least two metals are independently selected from zinc or group IIA metals, and Z is a metal selected from group IA metals of the Periodic Table.

4. The triple metal salts as claimed in claims 1 or 2, wherein group IIA metals are independently selected from Be, Mg, Ca, Sr, Ba or Ra in the form of their carbonates, oxides or hydroxides.

5. The triple metal salts as claimed in claims 1 or 2, wherein group IA metals are selected from Li, Na, K, Rb, Cs or Fr in the form of carbonates of hydroxides.

6. The triple metal salts as claimed in claim 1, further comprising 50 to 75% of HCA, 0 to 0.5% of lactone, 3 to 8% of calcium, 1 to 5% of magnesium, and 8 to 20% of potassium.

7. A process for preparing triple metal salts of (−)-hydroxycitric acid of the formula 1

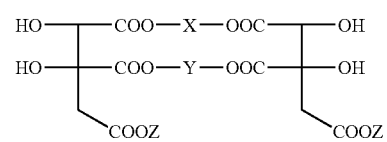

which comprises the slow addition 0.5 molar equivalent of group IIA metal compound to the purified aqueous extract of hydroxycitric acid followed by the addition of other group IIA 0.5 molar equivalent of metal compound and 1 molar equivalent of group IA metal compound.

8. A process for the preparation of triple salts of HCA comprising reacting a suspension of calcium hydroxycitrate with aqueous magnesium carbonate followed by aqueous potassium hydroxide solution.

9. A process for the preparation of triple salts of HCA comprising reacting an aqueous tripotassium hydroxycitrate with equimolar amounts of calcium hydroxycitrate and magnesium hydroxycitrate.

10. The processes as claimed in any one of claims 7, 8 and 9, wherein the metal compounds are hydroxides, oxides and carbonates of calcium, zinc or magnesium and potassium.

11. The process as claimed in any one of claims 7, 8 and 9, wherein said triple salt is separated from the reaction mixture by adding water miscible solvents and filtering or by spray drying the aqueous solution.

12. The process as claimed in claim 11, wherein said water miscible solvents are alcohols, acetone, acetonitrile, dioxan, tetrahydrofuran or mixtures thereof.

13. A therapeutic formulation containing triple salts of HCA as claimed in claim 1, for treating obesity.

14. A dietary or nutraceutical formulation containing triple metal salts of (−)-HCA as claimed in claim 1.

15. A beverage containing triple metal salts of (−)-HCA as claimed in claim 1.

* * * * *